US012749569B2

(12) United States Patent
Chen et al.

(10) Patent No.: US 12,749,569 B2
(45) Date of Patent: Sep. 29, 2026

(54) AUTOMATED DEVICE MAINTENANCE SUPPORT TOOL

(71) Applicant: CareFusion 303, Inc., San Diego, CA (US)

(72) Inventors: Evan Chen, San Diego, CA (US); Igor Nesterenko, San Diego, CA (US); Tiffany Hamrick, Carlsbad, CA (US); Michael Workman, Carlsbad, CA (US); Brian Sullivan, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 560 days.

(21) Appl. No.: 17/928,267

(22) PCT Filed: May 27, 2021

(86) PCT No.: PCT/US2021/034600

§ 371 (c)(1),
(2) Date: Nov. 28, 2022

(87) PCT Pub. No.: WO2021/243068

PCT Pub. Date: Dec. 2, 2021

(65) Prior Publication Data

US 2023/0215555 A1 Jul. 6, 2023

Related U.S. Application Data

(60) Provisional application No. 63/032,309, filed on May 29, 2020.

(51) Int. Cl.
*G16H 40/40* (2018.01)
*G16H 20/17* (2018.01)

(52) U.S. Cl.
CPC ............. *G16H 40/40* (2018.01); *G16H 20/17* (2018.01)

(58) Field of Classification Search
CPC ............................... G16H 40/40; G16H 20/17
(Continued)

(56) References Cited

U.S. PATENT DOCUMENTS 5,713,856 A 2/1998 Eggers et al.
7,124,059 B2 10/2006 Wetzer et al.
(Continued)

FOREIGN PATENT DOCUMENTS

EP 3540741 A1 * 9/2019 ............. G16H 40/20
WO WO-2006098927 A1 * 9/2006 .......... A61M 5/1413

OTHER PUBLICATIONS

International Search Report and Written Opinion of International Application No. PCT/US2021/034600, dated Sep. 8, 2021, 12 pages.

(Continued)

*Primary Examiner* — Jason B Dunham
*Assistant Examiner* — Kimberly A. Sass
(74) *Attorney, Agent, or Firm* — MASCHOFF BRENNAN

(57) ABSTRACT

A medical device is configured to detect, based on a reading from the sensor, a state of a first component of the plurality of electronic components, identify a maintenance requirement of the medical device based on the detected state of the first component, restrict a first function of the medical device based on the identified maintenance requirement, transmit the identified maintenance requirement to a server system, receive from the server system an instruction addressing the identified maintenance requirement, receiving a first access request, determine that the first access request is a maintenance access request, and in response to the maintenance (Continued)

access request, display the instruction on a user interface of the medical device.

20 Claims, 5 Drawing Sheets

(58) Field of Classification Search
USPC .............................................................. 705/2
See application file for complete search history.

(56) References Cited

U.S. PATENT DOCUMENTS

2009/0315510 A1* 12/2009 Dos Santos ............. H02J 50/80 320/165
2011/0028885 A1* 2/2011 Eggers ................... G16H 40/67 235/375
2013/0339039 A1* 12/2013 Roman .................. G06V 20/64 705/2
2014/0266713 A1 9/2014 Sehgal et al.
2015/0300923 A1* 10/2015 Halbert .................... G07C 3/00 702/122
2015/0371198 A1 12/2015 Jensen et al.
2017/0068792 A1* 3/2017 Reiner ............... A61B 17/1214

OTHER PUBLICATIONS

International Preliminary Report on Patentability from the International Preliminary Examining Authority for Application No. PCT/US2021/034600, dated Sep. 7, 2022, 21 pages.
Written Opinion from the International Preliminary Examining Authority for Application No. PCT/US2021/034600, dated May 31, 2022, 8 pages.
United Kingdom Office Action for Application No. GB2219832.9, dated Jul. 28, 2025, 3 pages.
Australian Office Action for Application No. 2021279058, dated May 12, 2026, 4 pages.
Canadian Office Action for Application No. 3,179,779, Apr. 21, 2026, 9 pages.

* cited by examiner

AUTOMATED DEVICE MAINTENANCE SUPPORT TOOL

CROSS-REFERENCE TO RELATED APPLICATION(S)

This application is a non-provisional of and claims priority to U.S. Provisional Patent Application No. 63/032,309 filed on May 29, 2020, entitled "AUTOMATED DEVICE MAINTENANCE SUPPORT TOOL" the entirety of which is incorporated herein by reference.

TECHNICAL FIELD

This application relates generally to a maintenance support tool for network-connected medical devices.

BACKGROUND

Medical devices typically require proactive maintenance according to manufacturer-specified schedules and reactive maintenance when components malfunction. For some medical devices, such as infusion pumps, the maintenance process can be cumbersome. A technician typically moves the devices to a maintenance setting, thereby taking the devices out of service. The technician performs maintenance, sometimes replacing parts that do not need to be replaced, affixes stickers with dates that need to be manually tracked, and eventually returns the devices to their respective locations in the healthcare setting.

Since healthcare organizations often implement networks of medical devices that require unique maintenance needs on differing schedules, the task of maintaining these medical devices grows more cumbersome as the number and complexity of such medical devices increase. As such, there is a need for a more efficient and effective maintenance solution for medical devices.

SUMMARY

Maintaining dozens of medical devices for use on a healthcare network is arduous and time consuming. Several concerns for healthcare organizations include reducing the amount of time medical devices are removed from service due to maintenance needs and reducing the amount of unnecessary component replacements while optimizing maintenance schedules and simplifying asset tracking.

Accordingly, there is a need for methods and systems that more efficiently maintain medical devices without removing them from service for longer than necessary. Disclosed implementations are able to automatically identify maintenance needs, restrict affected functionality of medical devices without completely removing them from service, and support technicians during maintenance procedures.

The disclosed subject matter relates to a method for maintaining a network-connected medical device. In accordance with some implementations, the method includes detecting a state of a component of the medical device (e.g., a battery) based on a sensor reading, and identifying a maintenance requirement of the medical device (e.g., a requirement to replace the battery) based on the detected state of the component. The method further includes restricting a function of the medical device (e.g., a high-power function) based on the identified maintenance requirement, while leaving other functions available for use. The medical device transmits the identified maintenance requirement to a server system and receives, from the server system, instructions addressing the identified maintenance requirement (e.g., a walkthrough detailing steps of a battery replacement to assist a technician). The medical device receives an access request (e.g., a user login), and upon determining that the access request is a maintenance access request (e.g., a technician logging in), the medical device displays the instructions on a user interface. In response to the maintenance requirement being satisfied (e.g., upon replacement of the battery), the restricted function is restored, and the medical device transmits, to the server system, a notification indicating that the maintenance requirement has been satisfied. Thus, the medical device remains at least partly operational while it awaits servicing, and since a technician can service the medical device on the spot, the medical device does not need to be moved to a maintenance setting, thereby increasing efficiency and optimizing the maintenance process. Other aspects include corresponding systems, apparatuses, and computer program products for implementation of the method.

According to various implementations, the disclosed system includes a medication delivery actuator; a sensor for monitoring at least a first component of the system; a transceiver; one or more processors communicatively coupled with the medication delivery actuator, sensor, and transceiver; and memory including instructions that, when executed by the one or more processors, cause the one or more processors to: detect, based on a reading from the sensor, a state of the first component; identify a maintenance requirement of the system based on the detected state of the first component; restrict a first function of the system based on the identified maintenance requirement; transmit, via the transceiver, the identified maintenance requirement to a server system; receive, from the server system via the transceiver, an instruction addressing the identified maintenance requirement; receive a request to access the system; determine that the request is a maintenance access request; and in response to the maintenance access request, display the instruction on a user interface of the system. Other aspects include corresponding methods, apparatuses, and computer program products for implementation of the system.

The disclosed subject matter also relates to a system for maintaining medical devices. The system includes one or more processors and a memory including instructions that, when executed by the one or more processors, cause the one or more processors to perform operations of the method as described herein. According to various implementations, the disclosed system includes one or more processors and a memory. The memory includes instructions stored thereon that, when executed by the one or more processors, cause the one or more processors to perform the method for maintaining a network-connected medical device. In some implementations, the one or more processors are communicatively coupled to a medication delivery actuator, a transceiver, and the sensor, wherein the sensor is configured to monitor at least the first component.

The disclosed subject matter also relates to a machine-readable medium embodying instructions that, when executed by a machine, allow the machine to perform a method for maintaining a medical device as described herein.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

DESCRIPTION OF IMPLEMENTATIONS

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Figure 1:
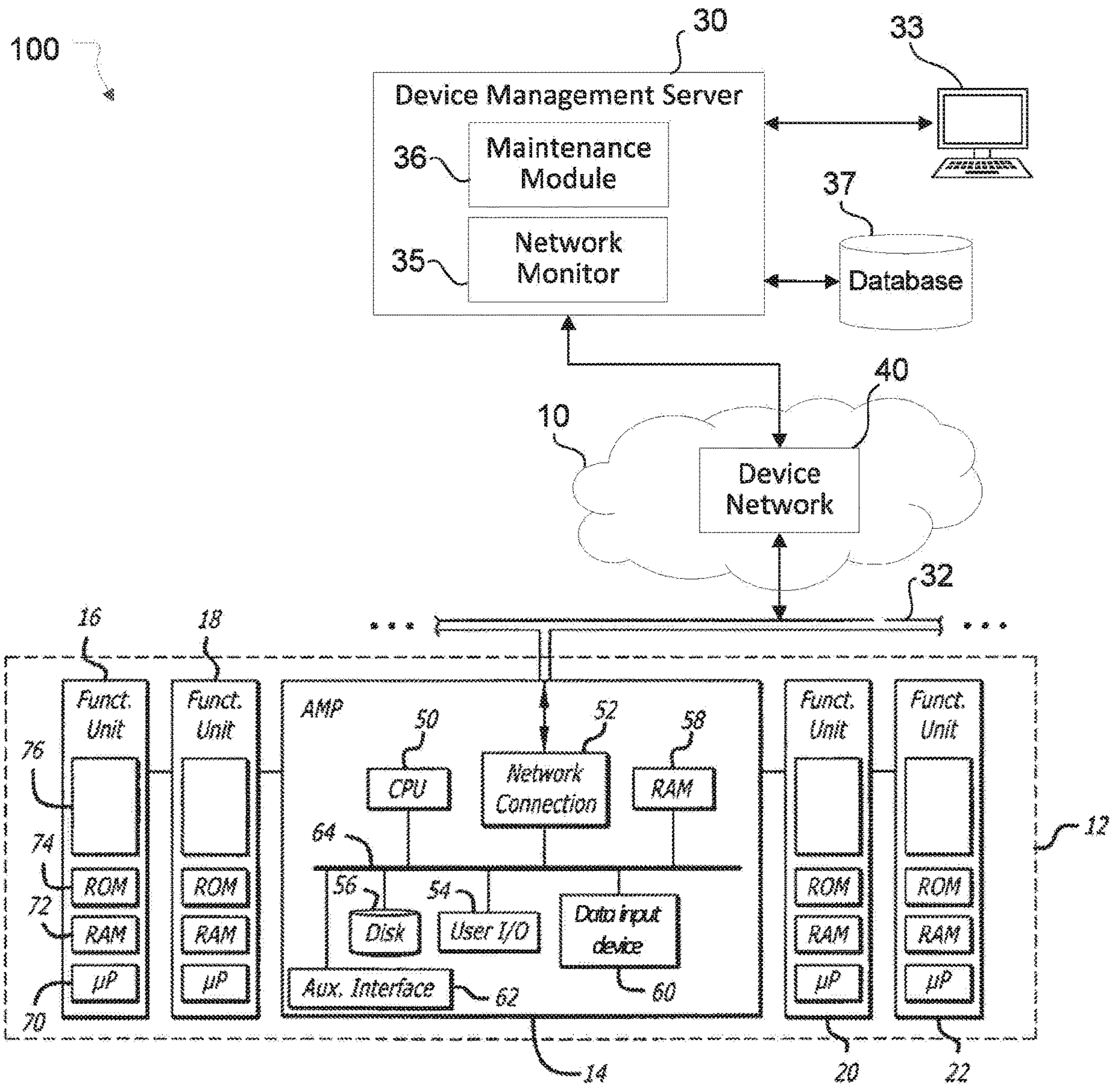
FIG. 1 depicts an example of a patient care system of a healthcare organization in accordance with aspects of the subject technology.

FIG. 1 depicts an example of an institutional patient care system 100 of a healthcare organization, according to aspects of the subject technology. In FIG. 1, a medical device 12 is connected to a hospital network 10. The term medical device may be used interchangeably with the term patient care device (or "PCD") or the term patient care unit (or "PCU"), any of which may include various medical devices such as an infusion pump, a vital signs monitor, a medicant dispensing device (e.g., cabinet, tote), a medication preparation device, an automated dispensing device, a module coupled with one of the aforementioned devices (e.g., a syringe pump module configured to attach to an infusion pump), or other similar devices. Each element 12 is connected to a healthcare network 10 by a transmission channel 32. Transmission channel 32 is any wired or wireless transmission channel, for example an 802.11 wireless local area network (LAN). In some implementations, network 10 also includes computer systems located in various departments throughout a hospital. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 40 by which medical devices 12 (and other devices) communicate in accordance with normal operations. According to some implementations, the devices and supporting services of network 10 or a portion thereof may be cloud-based with, for example, the servers and services (e.g., databases, APIs, etc.) may be remotely located from the hospital and/or distributed across multiple remote locations or regions.

Additionally, institutional patient care system 100 may incorporate a separate device management server 30 including a network monitor 35 and a maintenance module 36 in communication with a database 37. Moreover, although the device management server 30 is shown as a separate server, the functions and programming of the device management server 30 may be incorporated into another computer, such as, for example, a hospital information system server or cloud-based server, if such is desired by engineers designing the institution's information system. Institutional patient care system 100 may further include one or multiple device terminals 33 for connecting and communicating with device management server 30. Device terminals 33 may include personal computers, personal data assistances, mobile devices such as laptops, tablet computers, augmented reality devices, or smartphones, configured with software for communications with device management server 30 via network 10.

Maintenance module 36 tracks the status and condition of a plurality of medical devices 12 included in the institutional patient care system 100. Status information for each medical device is stored in the database 37, including, for example, service needs, part failures, maintenance jobs, component replacement schedules (e.g., battery replacements), information regarding part ordering, inventory status, and so forth. Maintenance module 36 identifies specific device needs, reactive and/or proactive, for part repair, part ordering, and available inventory as well as preventative maintenance needs. In some implementations, maintenance module 36 causes a dashboard to be displayed on device terminals 33 associated with maintenance technicians. Using an action list, the dashboard indicates which devices need service and the location of such devices, as well as part ordering information and instructional information (e.g., videos) that may support the technician. Generally, maintenance module 36 manages workflow for maintenance technicians. Medical devices 12 register themselves and periodically send status updates to the device management server 30, which, via the maintenance module 36, prioritizes maintenance actions (e.g., battery replacements) and directs technicians to the locations of devices requiring maintenance. The maintenance module 36 prioritizes medical devices for maintenance based on one or more of: priority of the maintenance identified (e.g., safety critical maintenance versus routine service), the location of each device (e.g., identify clusters of devices within close proximity), availability of necessary part(s) for the maintenance (e.g., if part is not available, lower the priority or prioritize according to an expected availability date), and whether the device is being used or scheduled to be used (e.g., assigned to or reserved for a patient).

Medical device 12 comprises a system for providing patient care, such as that described in U.S. Pat. No. 5,713,856 to Eggers et al., which is incorporated herein by reference for that purpose. Medical device 12 may include or incorporate pumps, physiological monitors (e.g., heart rate, blood pressure, ECG, EEG, pulse oximeter, and other patient monitors), therapy devices, medication delivery actuators, and other drug delivery devices may be utilized according to the teachings set forth herein. In the depicted example, medical device 12 comprises a control unit 14, also referred to as a control module 14 and an interface unit 14, connected to one or more functional modules 16, 18, 20, 22. Control unit 14 includes a central processing unit (CPU) 50 connected to a memory, for example, random access memory (RAM) 58, and one or more interface devices such as user interface (UI) device 54, a coded data input device 60, a network connection 52 (e.g., radio, network card, or transceiver), and an auxiliary interface 62 for communicating with additional modules or devices. Control unit 14 also, although not necessarily, includes a main non-volatile storage unit 56, such as a hard disk drive or non-volatile flash memory, for storing software and data and one or more internal buses 64 for interconnecting the aforementioned elements.

In various implementations, UI device 54 is a touch screen for displaying information to a user and allowing a user to input information by touching defined areas of the screen. Additionally or in the alternative, UI device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading magnetic strips, radio-frequency identification (RFID) devices whereby digital data encoded in RFID tags or smart labels are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, UI device 54 and data input device 60 may be the same device. Although data input device 60 is shown in FIG. 1 to be disposed within control unit 14, it is recognized that data input device 60 may be integral within a pharmacy system or located externally and communicating with a pharmacy system through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 16, 18, 20 and 22, and configured to communicate with control unit 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices associated with control unit 14 for providing care to a patient or for monitoring patient condition. As shown in FIG. 1, at least one of functional modules 16, 18, 20, 22 may be an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 18, 20 and/or 22 may be a printer, scanner, bar code reader or any other peripheral input, output or input/output device.

Each functional module 16, 18, 20, 22 communicates directly or indirectly with control unit 14, with control unit 14 providing overall monitoring and control of device 12. Functional modules 16, 18, 20, 22 may be connected physically and electronically in serial fashion to one or both ends of control unit 14 as shown in FIG. 1, or as detailed in Eggers et al. However, it is recognized that there are other means for connecting functional modules with the control unit 14 that may be utilized without departing from the subject technology. It will also be appreciated that devices such as pumps or patient monitoring devices that provide sufficient programmability and connectivity may be capable of operating as stand-alone devices and may communicate directly with the network without being connected through a separate control unit 14. As described above, additional medical devices or peripheral devices may be connected to medical device 12 through one or more auxiliary interfaces 62.

Each functional module 16, 18, 20, 22 may include module-specific components 76, a microprocessor 70, a volatile memory 72 and a nonvolatile memory 74 for storing information. In some implementations, a functional module may include hardware components similar to those of control unit 14 including, but not limited to, a CPU 50 connected to a memory, RAM 58, one or more interface devices such as UI device 54, a coded data input device 60, a network connection 52, and an auxiliary interface 62 for communicating with additional modules or devices. It should be noted that while four functional modules are shown in FIG. 1, any number of devices may be connected directly or indirectly to central control unit 14. The number and type of functional modules described herein are intended to be illustrative, and in no way limit the scope of the subject technology. Module-specific components 76 include any components necessary for operation of a particular module, such as a pumping mechanism for infusion pump module 16.

According to various implementations, while each functional module may be capable of independent operation (e.g., as described with respect to control unit 14 and its hardware components), control unit 14 is configured to monitor and control overall operation of device 12. For example, as will be described in more detail below, control unit 14 may provide programming instructions to the functional modules 16, 18, 20, 22 and monitor the status of each module.

Medical device 12 may be capable of operating in several different modes, or personalities, with each personality defined by a configuration database. A particular configuration database may be selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a medical device's 12 location in the hospital or hospital computer network 10. Patient care information may be entered through interface device 52, 54, 60 or 62, and may originate from anywhere in network 10, such as, for example, from a pharmacy server, admissions server, laboratory server, and the like.

Data to and from the various data sources can be converted into network-compatible data with existing technology, and movement of the information between the medical device and network can be accomplished by a variety of means. For example, medical device 12 and network 10 may communicate via automated interaction, manual interaction or a combination of both automated and manual interaction. Automated interaction may be continuous or intermittent and may occur through direct network connection 52 (as shown in FIG. 1), or through RS232 links, MIB systems, RF links such as BLUETOOTH, IR links, WLANS, digital cable systems, telephone modems or other wired or wireless communication means. Manual interaction between medical device 12 and network 10 involves physically transferring, intermittently or periodically, data between systems using, for example, UI device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in device management server 30, a decision support system, a remote data server, hospital department or unit stations, or within medical device 12 itself.

Figure 2:
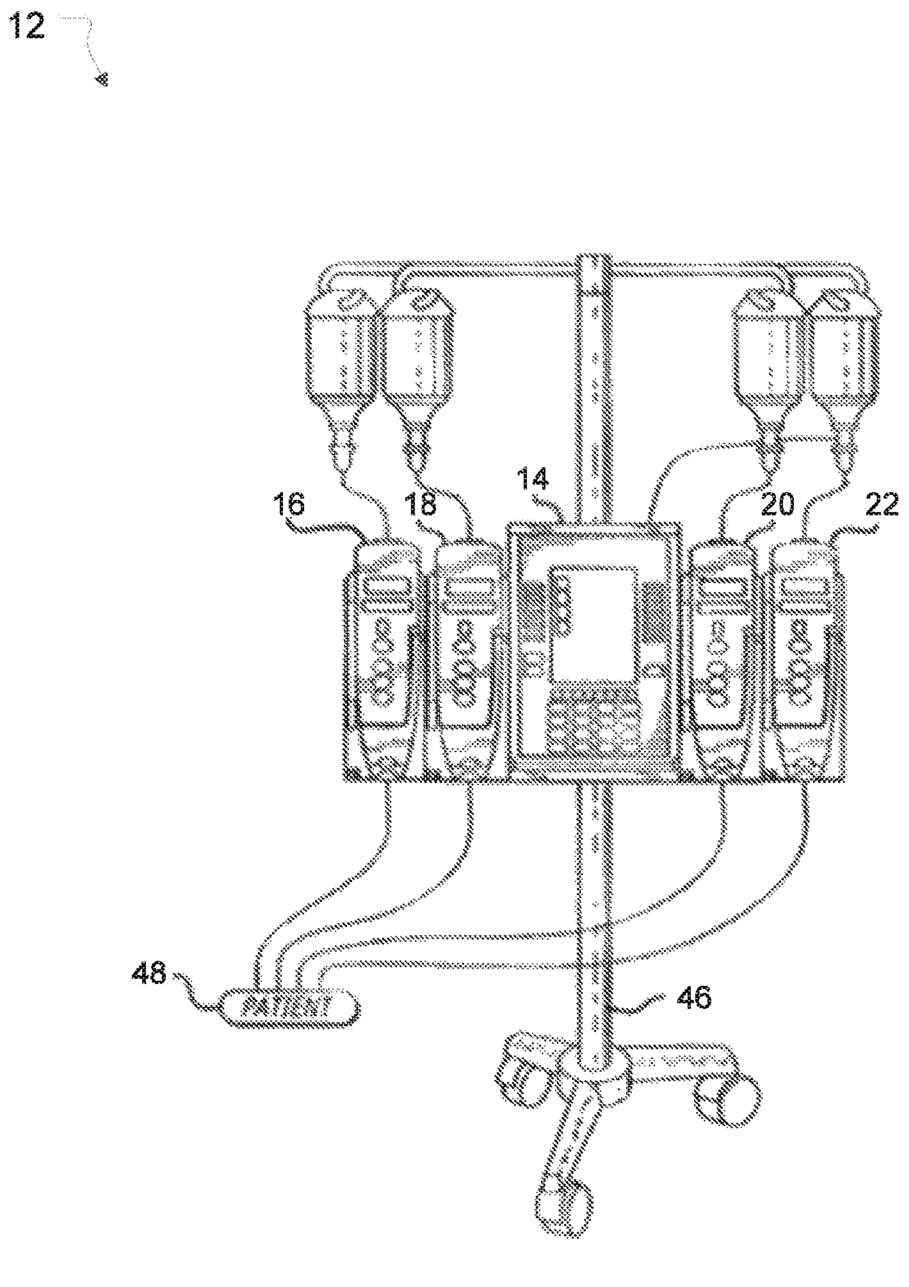
FIG. 2 depicts an example medical device in accordance with aspects of the subject technology.

FIG. 2 is an example medical device 12 which may be interacted with by a clinician within in a healthcare organization. Features shared with FIG. 1 are similarly numbered, and some are not further discussed for purposes of brevity. The medical device 12 shown in FIG. 2 may include one or more functional modules, such as the four fluid infusion pumps 16, 18, 20, and 22, each of which is in operative engagement with a respective fluid administration set. Fluid supplies, which may take various forms but in this case are shown as bottles, are inverted and suspended above the pumps. Fluid supplies may also take the form of bags or other types of containers. Both the medical device 12 and the fluid supplies are mounted to a roller stand or pole 46. As shown in the example implementation of FIG. 2, each fluid infusion pump administers fluid from a respective fluid supply to the same patient 48 so that the patient may receive the fluids in all of the fluid supplies. A separate infusion pump 16, 18, 20, and 22 may be used to infuse each of the fluids of the fluid supplies into the patient. The infusion pumps are flow control devices that act on respective tubes or fluid conduits to move fluid from the fluid supply through the conduit to the patient 48. Because individual pumps are used, each can be individually set to the pumping or operating parameters required for infusing the particular fluid from the respective fluid supply into the patient at the particular rate prescribed for that fluid by a clinician. Typically, medical fluid administration sets have more parts than are shown in FIG. 2. Many have check valves, drip chambers, valved ports, connectors, and other devices well known to those skilled in the art. These other devices have not been included in the drawings so as to preserve clarity of illustration.

Figure 3:
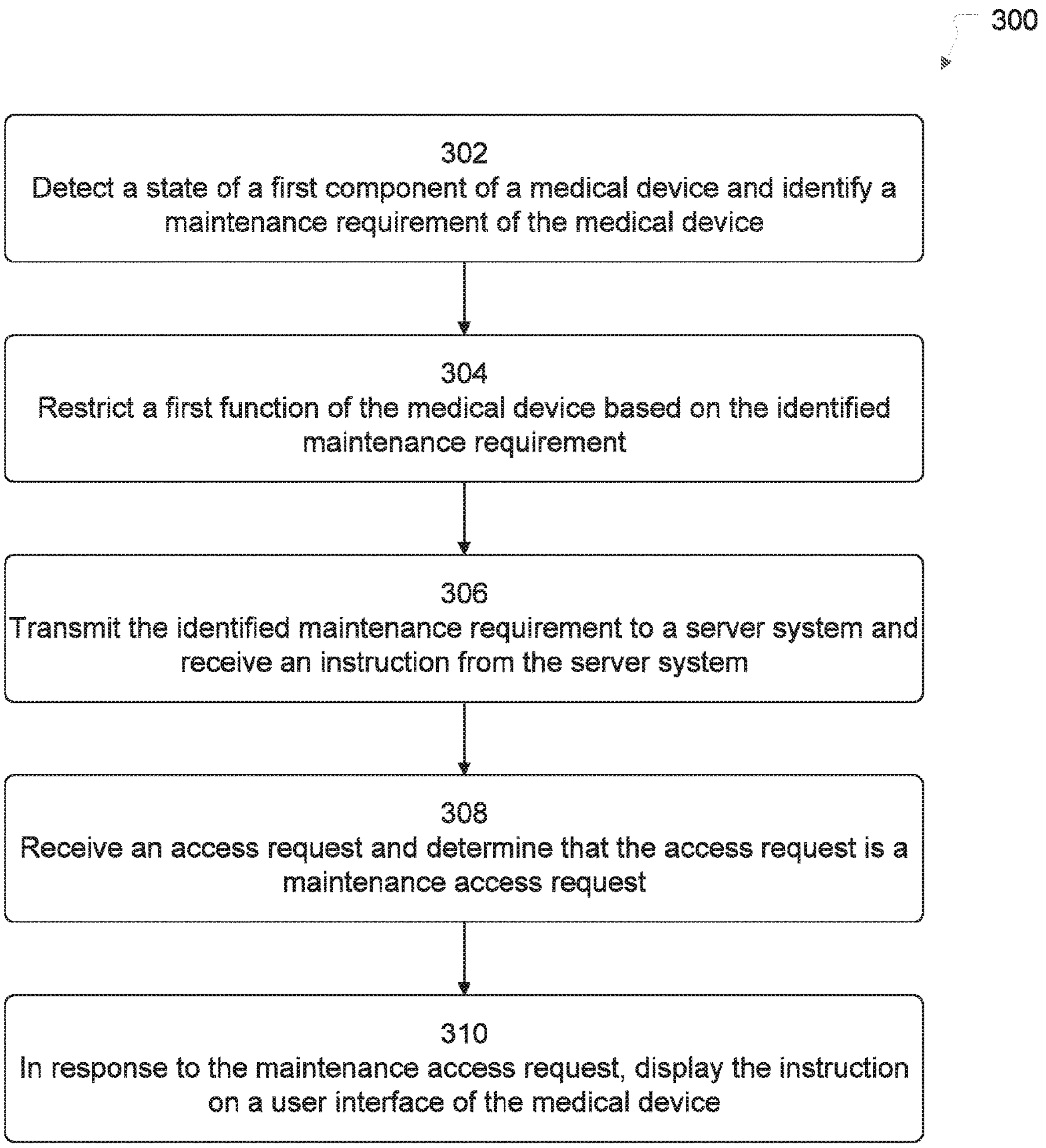
FIG. 3 depicts an example medical device maintenance process in accordance with aspects of the subject technology.

FIG. 3 depicts an example maintenance process for a network-connected medical device, according to aspects of the subject technology. For explanatory purposes, the various blocks of example process 300 are described herein with reference to FIGS. 1 and 2, and the components and/or processes described herein. One or more of the blocks of process 300 may be implemented, for example, by one or more computing devices including, for example, control unit 14, functional module included in the medical device (e.g., functional module 20 or 22), device management server 30, and/or other computing devices within patient care system 100. In some implementations, one or more of the blocks may be implemented apart from other blocks, and by one or more different processors or devices. Further, for explanatory purposes, the blocks of example process 300 are described as occurring in serial, or linearly. However, multiple blocks of example process 300 may occur in parallel. In addition, the blocks of example process 300 need not be performed in the order shown and/or one or more of the blocks of example process 300 need not be performed.

In the depicted example, a medical device (e.g., medical device 12) includes a sensor and a plurality of electronic components (e.g., module-specific components 76). Example electronic components include a battery, a wireless network interface (e.g., network connection 52), a radio-frequency identification (RFID) reader (e.g., data input device 60), and a pumping mechanism (e.g., when the medical device is, or otherwise includes, an infusion pump). Example sensors include a battery capacity sensor (e.g., configured to sense the battery's state of charge over time for the purpose of battery life determinations), a wireless communication sensor (e.g., configured to detect network connection deficiencies), a door sensor configured to detect one or more physical properties of the door such as number of times opened or quantity of bias force applied when the door is closed, an interconnection sensor to detect one or more properties of the physical connection (e.g., number of time attached or detached, electrical signal strength, bias force if the connection includes a biased member) between a functional module and the control unit or other functional module, a data input sensor (e.g., configured to detect RFID reader deficiencies), a clock to track one or more durations corresponding to different operational statuses of the medical device (e.g., time powered on, time in stand by, time infusing, time connected, etc.), a pump force sensor (e.g., configured to monitor the force applied by a pumping mechanism), and a motor sensor (e.g., configured to monitor motor revolutions of a pumping mechanism). It is noted that these examples are for illustrative purposes and are in no way meant to limit the scope of the subject disclosure. It is noted that these examples are for illustrative purposes and are in no way meant to limit the scope of the subject disclosure.

In some implementations, a sensor reading may include one or more capacity measurements of the battery (e.g., state of charge, state of health, internal resistance, charging rate, and/or discharging rate), and a processor (e.g., CPU 50) may determine, based on the one or more capacity measurements, that the battery needs to be replaced or repaired. In some implementations, a sensor reading may include one or more communication measurements of the wireless network interface (e.g., ping, jitter, packet loss, download speed, and/or upload speed), and a processor (e.g., CPU 50) may determine, based on the one or more communication measurements, that the wireless network interface needs to be replaced or repaired. In some implementations, a sensor reading may include one or more erroneous readings corresponding to the RFID reader (e.g., an unexpected reading and/or no readings for a threshold amount of time), and a processor (e.g., CPU 50) may determine, based on the one or more erroneous readings, that the RFID reader needs to be replaced or repaired. In some implementations, a sensor reading may include one or more motor revolution readings of the pumping mechanism (e.g., a number of motor revolutions in a predetermined amount of time), and a processor (e.g., CPU 50) may determine, based on the one or more motor revolution readings, that the pumping mechanism needs to be replaced or repaired. For example, the processor may determine that the pumping mechanism needs to be replaced or repaired based on a determination that the number of motor revolutions during a particular time period is lower than a threshold, higher than a threshold, or is otherwise not within an expected range. Additionally or alternatively, the processor may use a duration to identify the time period for specific maintenance activities. It is noted that these examples are for illustrative purposes and are in no way meant to limit the scope of the subject disclosure.

The medical device (e.g., CPU 50) detects (302), based on a reading from the sensor, a state of a first component of the plurality of electronic components. For example, the medical device detects a low battery state of charge based on a battery sensor reading, a malfunctioning wireless network interface, or a malfunctioning RFID reader. The medical device (e.g., CPU 50) identifies a maintenance requirement of the medical device based on the detected state of the first component. Example maintenance requirements include a battery replacement, a wireless network interface replacement, cleaning, safety testing, door or lock replacement, and an RFID reader replacement. Generally, the maintenance requirement comprises any action required to be undertaken by a technician in order to fix, secure, or otherwise improve the functioning of a component system (e.g., power, communications, access, pump, and the like) of the medical device.

The detection may be based on correspondence between one or more sensor readings and a threshold. For some detection, an individual sensor reading may be compared to the threshold. For some detection, a metric based on several sensor readings may be compared to the threshold. For example, a rate of change for the sensor values may be compared with the threshold. In some implementations, the one or more sensor readings may be provided to a machine learning model or other artificial intelligence representation to characterize the sensor readings and provide an actionable maintenance assessment of the readings. The threshold may be a static value stored in memory and associated with the condition or sensor. In some implementations, the threshold may be a dynamic value generated based on one or more values generated by or available to the medical device such as device uptime, device age, device model, firmware or software version executing on the device, device status (e.g., on, standby, infusing, healthcare mode, maintenance mode), or device location (e.g., care area).

The medical device (e.g., CPU 50) restricts or adjusts (304) a first function of the medical device based on the identified maintenance requirement. The adjustment may include generating a control message to change the state of the medical device. The adjustment may include restricting the first function. In this regard, certain features of the medical device may be disabled. For example, if the maintenance requirement includes a battery replacement due to a low capacity battery, the medical device may restrict a function requiring a fully charged battery (referred to as a high-power function). As another example, if the maintenance requirement includes replacement of the wireless network interface due to unreliable network communications, the medical device restricts the ability for a single clinician to sign off on a patient care procedure since the clinician's actions can no longer be double checked via the wireless network connection (e.g., by server 30). In this scenario, a second clinician would be required to provide secondary authorization for the first clinician's proposed patient care procedure. As another example, if the maintenance requirement includes replacement of a malfunctioning RFID reader, the medical device may restrict access to patient care functions requiring authentication of healthcare personnel. In this scenario, a healthcare clinician may be required to manually enter a passcode to gain access to the patient care functions. As another example, if the maintenance requirement includes replacing the pumping mechanism of an infusion pump, the medical device may restrict a pumping function of the infusion pump.

In some implementations, certain maintenance requirements may cause adjustment of the medical device to place limits on healthcare-related functions, such as drug-delivery. For example, in response to detecting a faulty flow sensor, an infusion device may limit patient infusions to certain classes of fluids or medications (e.g., saline-based and non-narcotic solutions). To bypass such limits, the medical device may require a secondary authorization from another clinician authorized to perform the procedure (e.g., administer a drug). Generally, when the medical device restricts certain functions based on the maintenance requirement, other functions may remain unrestricted (e.g., functions not requiring use of the component(s) subject to the maintenance requirement), thereby allowing the medical device to remain in service until a technician can address the maintenance requirement. Additional or alternative adjustments that may be applied include activating or deactivating a structural element of the controlled device such as a light, audio playback, a motor, a lock, a pump, a display, or other component of a device described herein.

The medical device (e.g., CPU 50) transmits (306) the identified maintenance requirement to a server system, such as a central repository for maintenance workflow (e.g., maintenance module 36 of device management server 30). The identified maintenance requirement may include, for example, an identification of the system or component requiring maintenance. For example, a part number may be transmitted to the server. The server system receives maintenance requirements from a plurality of medical devices, as described above with reference to maintenance module 36 (FIG. 1), and prioritizes the maintenance workflow for one or more technicians. As part of this workflow, the maintenance module 36 sends an alert to a technician (e.g., via terminal 33) to address the maintenance requirement of the medical device. In addition, the medical device receives, from the server system, an instruction addressing the maintenance requirement. For example, the instruction includes guidance for addressing the maintenance need (e.g., guidance for replacing the battery, such as a step-by-step replacement walk-through), and/or identification information (e.g., a part number or serial number) of a replacement for the first component (e.g., a serial number of the battery to be replaced and/or a serial number of the new battery to be installed). The guidance and/or identification information may be displayed on a user interface of the medical device (e.g., UI device 54).

In some implementations, the transmission at 306 may be optional. For example, if a maintenance requirement may be associated with a priority level. If the priority level corresponds to a level at which the maintenance is recommended but not essential for the medical device, the medical device may store the recommendation in a memory accessible by the medical device.

The medical device (e.g., CPU 50) receives (308) an access request and determines whether the access request is a maintenance access request (e.g., associated with a technician attempting to gain access to the medical device for maintenance purposes) or a healthcare access request (e.g., associated with a healthcare clinician attempting to gain access to the medical device for patient care purposes). For example, the access request comprises a login request detected by a badge swipe or a passcode (e.g., entered via data input device 60). In this scenario, if the badge or passcode is associated with a technician, the access request is determined to be a maintenance access request, and if the badge or passcode is associated with a healthcare clinician, the access request is determined to be a healthcare access request.

Based on the type of access request, the medical device operates in a particular mode. For example, in response to receiving a maintenance access request and granting maintenance access, the medical device (e.g., CPU 50) operates in a maintenance mode, in which patient care functions requiring healthcare personnel may be unavailable (except for the purpose of performing diagnostics). While operating in maintenance mode, the medical device displays (310) the instruction (e.g., the guidance and/or component identification information) on a user interface of the medical device (e.g., UI device 54).

The medical device may also operate in a healthcare mode. For example, in response to receiving a healthcare access request (e.g., prior to receiving the maintenance access request) and granting healthcare access, the medical device (e.g., CPU 50) operates in the healthcare mode, in which maintenance functions requiring a technician may be unavailable. While operating in healthcare mode, the medical device may make available one or more unrestricted patient care functions while continuing to restrict the functions restricted in operation 304 until the respective maintenance requirements are addressed. In some implementations, while in healthcare mode, the medical device (e.g., CPU 50) enables an additional function based on the restricted function. For example, if wireless communication functions are disabled, the medical device enables a feature for requiring a second healthcare clinician to double check patient care operations proposed by a first healthcare clinician. As another example, if the RFID reader is disabled, the medical device enables a feature for receiving manually entered input associated with patient care operations that otherwise would have been scanned by the RFID reader.

Maintenance module 36 detects when the identified maintenance requirement has been satisfied. Satisfaction of the maintenance requirement may be based on information sent directly from the medical device, or based on further evaluation of the medical device by maintenance module 36. For example, maintenance module 36 may periodically poll the medical device and other systems to determine if the maintenance requirement has been addressed. A technician may be required to login to the medical device or a server (e.g., maintenance module 36) through the medical device, or login to a device associated with the technician (e.g., a mobile device such as terminal 33), and indicate that remediation of the maintenance requirement has been initiated. As part of this process, the technician may be required to scan the part number identified as being the focus of the maintenance requirement. The maintenance requirement may then be satisfied based on receiving a proper login request by a technician designated to perform maintenance on the device (e.g., assigned to work on the device by module 36), an access code entered by the technician indicating that the maintenance was performed, and/or an indication that the part number identified as being the focus of the maintenance requirement was scanned by the technician. In some implementations, the system may receive. scan or otherwise obtain an identifier for a part previously installed in the medical device. In such implementations, receipt of the identifier for a previously installed part may be compared to a historical record for the device and/or a replacement part identifier to confirm the maintenance is complete. For example, if the new part is of a different type than the part removed, the system may prevent clearance of the maintenance requirement. Such features may reduce the likelihood of theft of parts for the medical device and ensure parts associated with the maintenance request are included.

When the technician has addressed the maintenance requirement (e.g., replaced the battery and/or addressed any other maintenance action items), the medical device (e.g., CPU 50) determines that the maintenance requirement has been satisfied (e.g., by performing a diagnostic based on a subsequent reading from the sensor). In response to the determination that the maintenance requirement has been satisfied, the medical device unrestricts the function that was restricted in operation 304, and transmits, to the server system, a notification indicating that the maintenance requirement has been satisfied.

In some implementations, the server system reserves the medical device (e.g., restricts access to healthcare personnel) upon receiving the maintenance requirement in operation 306, or upon determining that the technician is about to address the maintenance requirement, thereby ensuring that the medical device is available for servicing by the technician when the technician has arrived to address the maintenance requirement. As such, efficiency of the maintenance workflow is increased since the technician is prevented from having to wait for the medical device to be available for servicing and from having to return to the medical device multiple times. In these implementations, the medical device receives a reservation instruction from the server system (e.g., prior to receiving the maintenance access request). In response to the reservation instruction, the medical device restricts non-maintenance access to the medical device (e.g., restricts access by healthcare personnel). Subsequent to the maintenance actions performed by the technician, in response to the determination that the maintenance requirement has been satisfied, the medical device restores non-maintenance access to the medical device.

For implementations that store recommended maintenance for the medical device, upon detecting an access request by a user associated with a maintenance role, the medical device may present a list of one or more stored recommendations such as via a graphical user interface.

Operations of the above-described example 300 and related features and applications may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RANI chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 4:
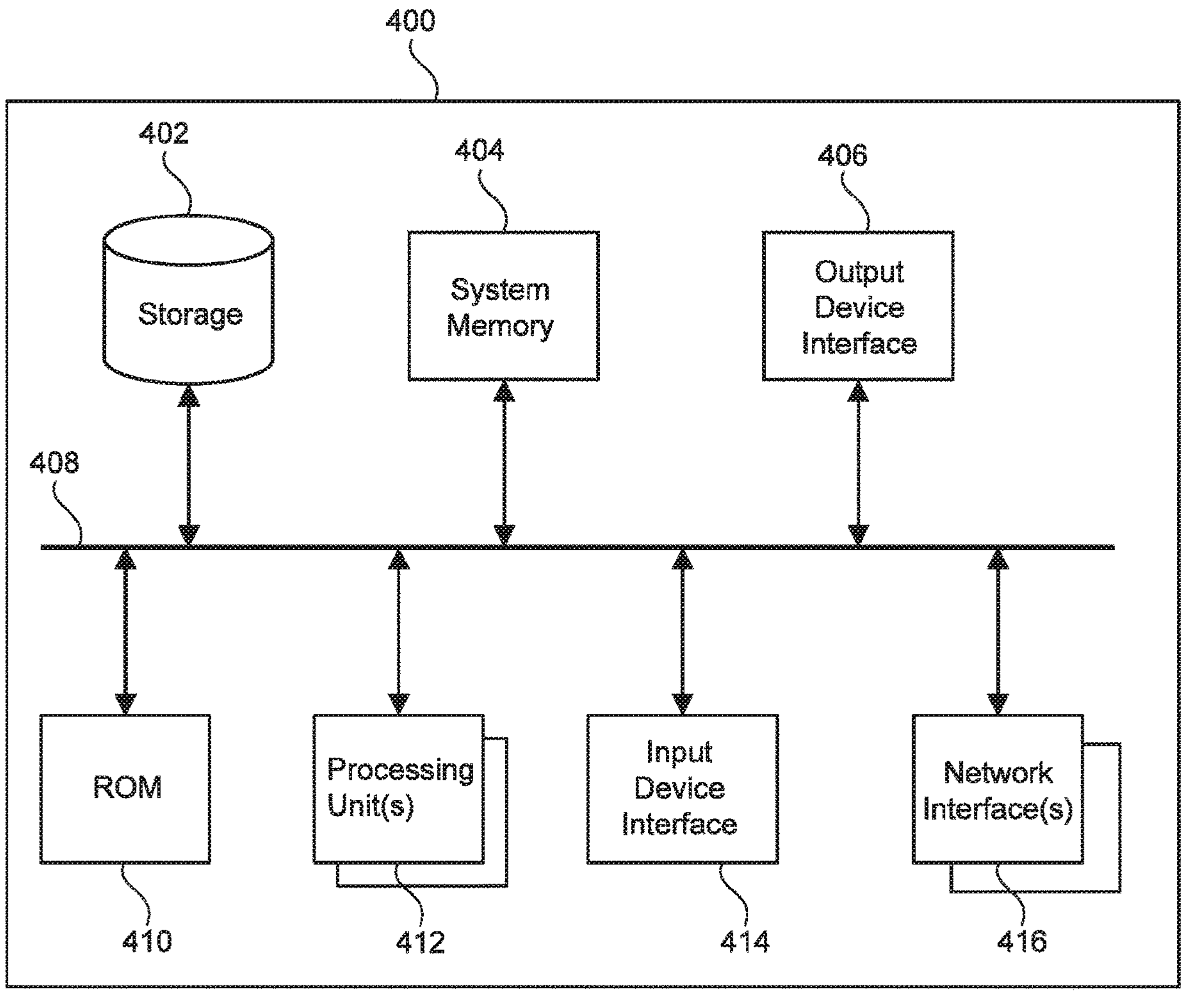
FIG. 4 is a conceptual diagram illustrating an example electronic system for the maintenance of medical devices in accordance with aspects of the subject technology.

FIG. 4 is a conceptual diagram illustrating an example electronic system 400 for maintaining medical devices, according to aspects of the subject technology. Electronic system 400 may be a computing device for execution of software associated with one or more portions or steps of process 300, or components and processes provided by FIGS. 1-3, including but not limited to device management server 30, computing hardware within medical device 12, or terminal device 33. Electronic system 400 may be representative, in combination with the disclosure regarding FIGS. 1-3. In this regard, electronic system 400 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 400 may include various types of computer readable media and interfaces for various other types of computer readable media. In the depicted example, electronic system 400 includes a bus 408, processing unit(s) 412, a system memory 404, a read-only memory (ROM) 410, a permanent storage device 402, an input device interface 414, an output device interface 406, and one or more network interfaces 416. In some implementations, electronic system 400 may include or be integrated with other computing devices or circuitry for operation of the various components and processes previously described.

Bus 408 collectively represents all system, peripheral, and chipset buses that communicatively connect the numerous internal devices of electronic system 400. For instance, bus 408 communicatively connects processing unit(s) 412 with ROM 410, system memory 404, and permanent storage device 402.

From these various memory units, processing unit(s) 412 retrieves instructions to execute and data to process in order to execute the processes of the subject disclosure. The processing unit(s) can be a single processor or a multi-core processor in different implementations.

ROM 410 stores static data and instructions that are needed by processing unit(s) 412 and other modules of the electronic system. Permanent storage device 402, on the other hand, is a read-and-write memory device. This device is a non-volatile memory unit that stores instructions and data even when electronic system 400 is off. Some implementations of the subject disclosure use a mass-storage device (such as a magnetic or optical disk and its corresponding disk drive) as permanent storage device 402.

Other implementations use a removable storage device (such as a floppy disk, flash drive, and its corresponding disk drive) as permanent storage device 402. Like permanent storage device 402, system memory 404 is a read-and-write memory device. However, unlike storage device 402, system memory 404 is a volatile read-and-write memory, such a random access memory. System memory 404 stores some of the instructions and data that the processor needs at runtime. In some implementations, the processes of the subject disclosure are stored in system memory 404, permanent storage device 402, and/or ROM 410. From these various memory units, processing unit(s) 412 retrieves instructions to execute and data to process in order to execute the processes of some implementations.

Bus 408 also connects to input and output device interfaces 414 and 406. Input device interface 414 enables the user to communicate information and select commands to the electronic system. Input devices used with input device interface 414 include, e.g., alphanumeric keyboards and pointing devices (also called "cursor control devices"). Output device interface 406 enables, e.g., the display of images generated by the electronic system 400. Output devices used with output device interface 406 include, e.g., printers and display devices, such as cathode ray tubes (CRT) or liquid crystal displays (LCD). Some implementations include devices such as a touchscreen that functions as both input and output devices.

Also, as shown in FIG. 4, bus 408 also couples electronic system 400 to a network (not shown) through network interfaces 416. Network interfaces 416 may include, e.g., a wireless access point (e.g., Bluetooth or WiFi) or radio circuitry for connecting to a wireless access point. Network interfaces 416 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 400 can be used in conjunction with the subject disclosure.

Figure 5:
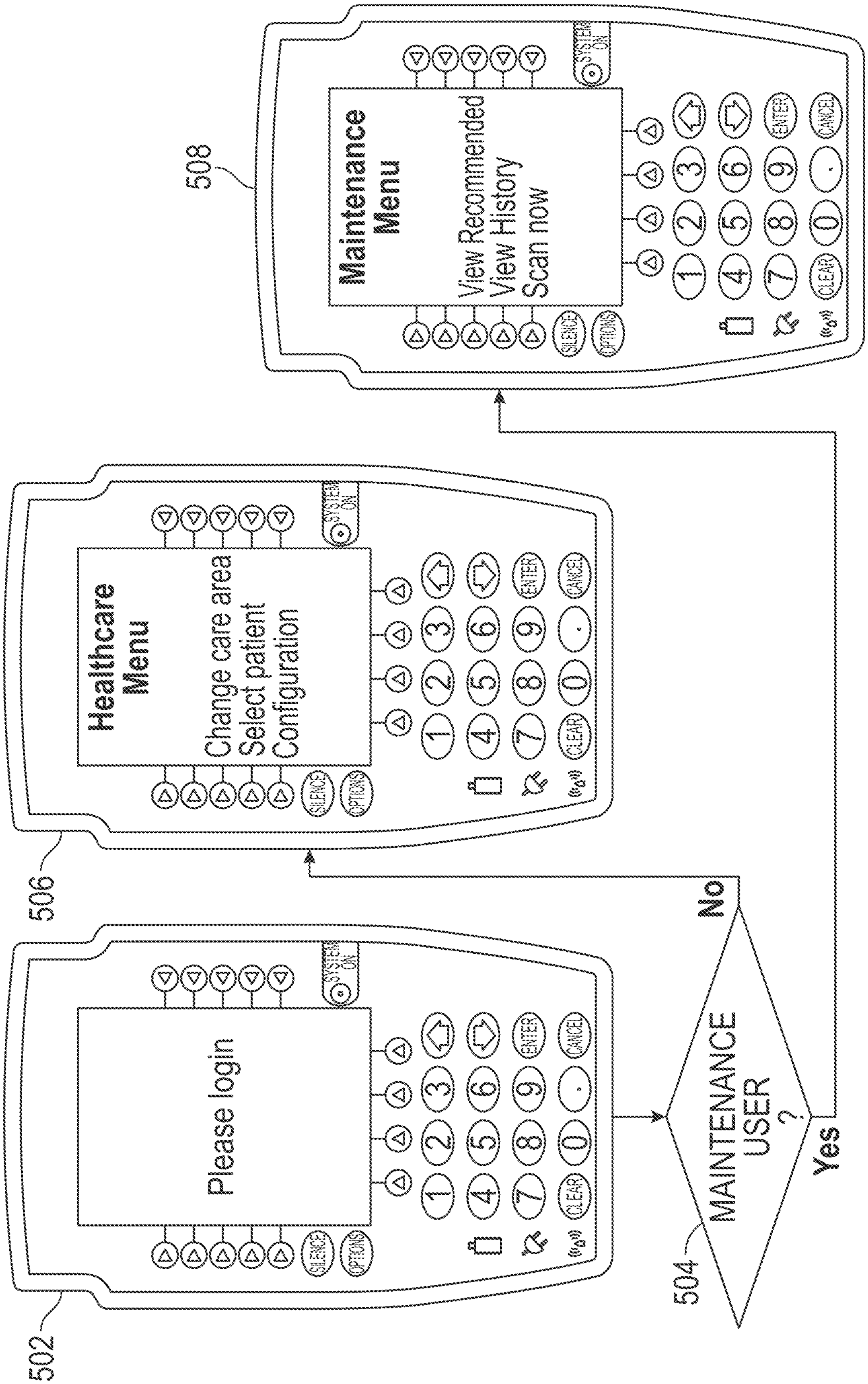
FIG. 5 is a conceptual diagram depicting an example transition between user interfaces for the maintenance support features described herein.

FIG. 5 is a conceptual diagram depicting an example transition between user interfaces for the maintenance support features described herein, according to aspects of the subject technology. It may be desirable to hide or disable certain features from general users and allow only authorized or specifically trained users to access such features. The hiding may be based on a patient safety and training concern. The hiding may be based on the desire to streamline the medical device to infer, based on a user's role, what feature(s) they may access.

At 502, the medical device may present an interface to receive user identification information. The medical device may receive the information directly such as via a user interface input, badge scan, barcode scan, or other input. In some implementations, the medical device may be communicatively coupled with another device that can collect or provide user information. One example of such a device is an electronic medical record (EMR) terminal.

At 504, the medical device may determine which role the identified user is associated with. The role may be stored locally at the medical device or may be provided from a user management system communicatively coupled with the medical device. If the user's role is a clinical role (e.g., patient caregiver), the medical device may adjust to a first mode and present the interface 506. The interface 506 may include options for providing care with the medical device such as selecting a care area, patient, or configuring the device for clinical use. The adjustment to the first mode may include additional or alternative control or configuration adjustments based on the identified maintenance for the medical device such as those described herein.

Returning to 504, if the role of the user is determined to be a maintenance user, the medical device may adjust into a second mode, different from the first mode, and present the interface 508. The interface 508 may include options for maintaining the medical device such as selecting viewing recommended maintenance, viewing a history of maintenance for the device, or initiating a scan for maintainable events at the device. The adjustment to the second mode may include additional or alternative control or configuration adjustments based on the identified maintenance for the medical device such as those described herein. Any maintenance events performed while the user is logged in, may be recorded in memory and associated with an identifier for the user. In this way, an audit of who made what changes to the medical device is generated.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some embodiments, a server transmits data (e.g., an HTML, page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of Subject Technology as Clauses:

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A system, comprising: a medication delivery actuator; a sensor for monitoring at least a first component of the system; a transceiver; one or more processors communicatively coupled with the medication delivery actuator, sensor, and transceiver; and memory including instructions that, when executed by the one or more processors, cause the one or more processors to: detect, based on a reading from the sensor, a state of the first component; identify a maintenance requirement of the system based on the detected state of the first component; restrict a first function of the system based on the identified maintenance requirement; transmit, via the transceiver, the identified maintenance requirement to a server system; receive, from the server system via the transceiver, an instruction addressing the identified maintenance requirement; receive a request to access the system; determine that the request is a maintenance access request; and in response to the maintenance access request, display the instruction on a user interface of the system.

Clause 2. The system of Clause 1, wherein the memory includes instructions to further cause the one or more processors to: determine, based on a subsequent reading from the sensor, that the maintenance requirement has been satisfied; and in response to the determination that the maintenance requirement has been satisfied: unrestrict the first function of the system; and transmit, to the server system, a notification indicating that the maintenance requirement has been satisfied.

Clause 3. The system of Clause 2, wherein the maintenance access request includes an identifier for a user; and wherein the memory includes instructions to further cause the one or more processors to: include the identifier in the notification.

Clause 4. The system of any of the preceding clauses, wherein the system comprises an infusion pump.

Clause 5. The system of any of the preceding clauses, wherein the memory includes instructions to further cause the one or more processors to: prior to receiving the request to access the system: receiving a reservation instruction from the server system; restricting non-maintenance access to the system; and in response to the determination that the maintenance requirement has been satisfied: unrestricting non-maintenance access to the systems.

Clause 6. The system of any of the preceding clauses, wherein the memory includes instructions to further cause the one or more processors to: receive, via a scanning device associated with the system, a first part identifier to be installed in the system; determine that the first part identifier is authorized for the maintenance requirement; and cause presentation of a perceivable indicator that a part associated with the first part identifier is authorized.

Clause 7. The system of Clause 6, wherein the memory includes instructions to further cause the one or more processors to: receive, via the scanning device, a second part identifier to be removed from the system; determine that the second part identifier: (i) was previously installed in the system; and (ii) is associated with the maintenance requirement; and indicate the maintenance requirement is satisfied.

8. A method, comprising: at a medical device including a sensor and a plurality of electronic components: detecting, based on a reading from the sensor, a state of a first component of the plurality of electronic components; identifying a maintenance requirement of the medical device based on the detected state of the first component; restricting a first function of the medical device based on the identified maintenance requirement; transmitting the identified maintenance requirement to a server system; receiving, from the server system, an instruction addressing the identified maintenance requirement; receiving a first access request; determining that the first access request is a maintenance access request; and in response to the maintenance access request, displaying the instruction on a user interface of the medical device.

Clause 9. The method of Clause 8, further comprising: receiving an access request prior to receiving the maintenance access request; determining that the prior access request is a healthcare access request; and, in response to the healthcare access request, enabling a second function of the medical device based on the restricted first function of the medical device.

Clause 10. The method of Clause 9, wherein the second function of the medical device is a secondary authorization requirement for a patient care procedure.

Clause 11. The method of any of Clauses 8 through 10, further comprising: determining, based on a subsequent reading from the sensor, that the maintenance requirement has been satisfied; and in response to the determination that the maintenance requirement has been satisfied: unrestricting the first function of the medical device; and transmitting, to the server system, a notification indicating that the maintenance requirement has been satisfied.

Clause 12. The method of Clause 11, further comprising: prior to receiving the first access request: receiving a reservation instruction from the server system; restricting non-maintenance access to the medical device; and in response to the determination that the maintenance requirement has been satisfied: unrestricting non-maintenance access to the medical device.

Clause 13. The method of any of Clauses 8 through 12, wherein: the first component is a battery; the identified maintenance requirement comprises a battery replacement; and the first function is a high-power function of the medical device.

Clause 14. The method of any of Clauses 8 through 12, wherein: the first component is a wireless network interface; the identified maintenance requirement comprises a wireless network interface replacement; and the first function is a service sign-off function of the medical device.

Clause 15. The method of any of Clauses 8 through 12, wherein: the first component is a radio-frequency identification (RFID) reader; the identified maintenance requirement comprises an RFID reader replacement; and the first function is an access request function of the medical device.

Clause 16. The method of any of Clauses 8 through 12, wherein: the first component is a pumping mechanism; the identified maintenance requirement comprises a pumping mechanism replacement; and the first function is a pumping function of the medical device.

Clause 17. The method of any of Clauses 8 through 16, wherein the instruction includes: guidance for replacing the first component; and identification information of a replacement for the first component.

Clause 18. The method of any of Clauses 8 through 17, wherein the first access request comprises a login request detected by a badge swipe or a passcode.

Clause 19. The method of Clause 18, wherein determining that the first access request is a maintenance access request includes determining that the first access request comprises a login request detected by a badge or passcode associated with a maintenance technician.

Clause 20. A non-transitory machine-readable storage medium embodying instructions that, when executed by a machine, allow the machine to perform a method, the method comprising one or more of the operations of Clauses 8 through 19.

Clause 21. A system, comprising one or more processors and a memory including instructions that, when executed by the one or more processors, cause the one or more processors to perform the method of any of Clauses 8 through 19.

Clause 22. The system of Clause 21, wherein the one or more processors are communicatively coupled to a medication delivery actuator, a transceiver, and the sensor, wherein the sensor is configured to monitor at least the first component.

Further Consideration:

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, C, C++, web services, or rich site summary (RSS). In some embodiments, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

As used herein, the terms "control" or "controlling" or "adjust" or "adjusting" encompass a wide variety of actions. For example, "controlling" a device may include transmitting one or more messages to adjust an operational state or functional element of the device. The message may include specific instructions to be executed by a processor of the device to manifest the change. The "controlling" may include storing a value in a location of a storage device for subsequent retrieval by the device to be controlled, transmitting a value directly to the device to be controlled via at least one wired or wireless communication medium, transmitting or storing a reference to a value, and the like. For example, a control message may include a value to adjust a level of power from a power source of the controlled device. As another example, a control message may activate or deactivate a structural element of the controlled device such as a light, audio playback, a motor, a lock, a pump, a display, or other component of a device described herein. "Controlling" may include indirect control of the device by adjusting a configuration value used by the controlled device. For example, the control message may include a threshold value for a device characteristic (e.g., temperature, rate, frequency, etc.). The threshold value may be stored in a memory location and referred to by the controlled device during operation.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

What is claimed is:

1. A system for maintaining an infusion device, comprising:

a sensor configured to monitor a component of a plurality of electronic components of the infusion device;

a transceiver;

one or more processors communicatively coupled with the transceiver; and memory including instructions that, when executed by the one or more processors, cause the one or more processors to:

obtain a reading from the sensor;

detect, based on the reading from the sensor, a state of the component;

identify, based on the detected state of the component, a maintenance requirement comprising an action to be undertaken by a technician to improve functioning of a component system pertaining to the component;

restrict, responsive to identifying the maintenance requirement, one or more features of the infusion device, including disabling a function of the component, based on the identified maintenance requirement, while maintaining operation of other patient care functions of the infusion device;

transmit, via the transceiver over a network, the identified maintenance requirement to a server and an identification of the component;

receive, from the server over the network via the transceiver, component identification information identifying a replacement part for replacement of the component and guidance for performing maintenance on the system to address the identified maintenance requirement with the replacement part;

receive, after the one or more features of the infusion device is restricted, an access request of a user to access the infusion device;

determine, based on the access request, whether the access request is associated with a technician attempting to gain access to the infusion device for maintenance purposes or a clinician attempting to gain access to the infusion device for patient care purposes; and adjust the infusion device to one of a healthcare mode and a maintenance mode responsive to the access request, wherein the one or more processors are further caused to, after the infusion device is adjusted:

responsive to the access request being associated with a technician for maintenance purposes: operate the infusion device in a maintenance mode that restricts patient care functions including operation of a pump or physiological monitor by a user, display the component identification information and the guidance for performing the maintenance with the replacement part on a first user interface of the system, and prevent clearance of the identified maintenance requirement until an identifier for the replacement part is received; and responsive to the access request being associated with the clinician for patient care purposes: operate the infusion device in a healthcare mode that restricts the patient care functions associated with the identified maintenance requirement while patient care functions not requiring use of the component are unrestricted, display options for providing care with the infusion device on a second user interface of the infusion device different than the first user interface and, while in the healthcare mode, disable the maintenance mode to prevent display of the component identification information and the guidance to the user.

2. The system of claim 1, wherein the memory includes instructions to further cause the one or more processors to:

determine, based on a subsequent reading from the sensor, that the maintenance requirement has been satisfied; and in response to the determination that the maintenance requirement has been satisfied:

unrestrict the one or more features of the infusion device; and transmit, to the server, a notification indicating that the maintenance requirement has been satisfied.

3. The system of claim 2, wherein the access request includes an identifier for the user; and wherein the memory includes instructions to further cause the one or more processors to: include the identifier in the notification.

4. The system of claim 1, wherein the system comprises an infusion pump and the infusion device is the infusion pump.

5. The system of claim 1, wherein the access request is associated with the technician for maintenance purposes, and wherein the memory includes instructions to further cause the one or more processors to:

prior to receiving the access request associated with the technician for maintenance purposes:

receiving a reservation instruction from the server;

restricting access to the infusion device for maintenance purposes only; and in response to a determination that the maintenance requirement has been satisfied:

unrestricting non-maintenance access to the infusion device.

6. The system of claim 1, wherein the memory includes instructions to further cause the one or more processors to:

receive, via a scanning device associated with the system, a first part identifier to be installed in the system;

determine that the first part identifier is authorized for the maintenance requirement; and cause presentation of a perceivable indicator that a part associated with the first part identifier is authorized.

7. The system of claim 6, wherein the memory includes instructions to further cause the one or more processors to:

receive, via the scanning device, a second part identifier to be removed from the system;

determine that the second part identifier: (i) was previously installed in the system; and (ii) is associated with the maintenance requirement; and indicate the maintenance requirement is satisfied.

8. A method comprising, at an infusion device including a sensor and a plurality of electronic components:

obtaining a reading from a sensor associated with an infusion device;

detecting, based on the reading from the sensor, a state of a component of the plurality of electronic components;

identifying, based on the detected state of the component, a maintenance requirement of the infusion device and comprising an action to be undertaken by a technician to improve functioning of a component system pertaining to the component;

restricting, responsive to identifying the maintenance requirement, one or more features of the infusion device, including disabling a first function of the component, based on the identified maintenance requirement, while maintaining operation of other patient care functions of the infusion device;

transmitting the identified maintenance requirement and an identification of a the component to a server over a network;

receiving, from the server over the network, component identification information identifying a replacement part for replacement of the component and guidance for performing maintenance on the infusion device to address the identified maintenance requirement with the replacement part;

receiving, after the one or more features of the infusion device is restricted, a first access request of a user;

determining, based on the first access request, whether the first access request is associated with a technician attempting to gain access to the infusion device for maintenance purposes or a clinician attempting to gain access to the infusion device for patient care purposes; and adjusting the infusion device to one of a healthcare mode and a maintenance mode responsive to the first access request, wherein the method further comprises, after the infusion device is adjusted:

responsive to the first access request being associated with a technician for maintenance purposes: operating the infusion device in a maintenance mode that restricts patient care functions including operation of a pump or physiological monitor by the user, display the component identification information and the guidance for performing the maintenance with the replacement part on a first user interface of the infusion device, and prevent clearance of the identified maintenance requirement until an identifier for the replacement part is received;

responsive to the first access request being associated with the clinician for patient care purposes: operating the infusion device in a healthcare mode that restricts the patient care functions associated with the identified maintenance requirement while patient care functions not requiring use of the component are unrestricted, and display options for providing care with the infusion device on a second user interface of the infusion device different than the first user interface and, while in the healthcare mode, disable the maintenance mode to prevent display of the component identification information and the guidance to the user.

9. The method of claim 8, further comprising:

receiving a prior access request prior to receiving the first access request associated with the technician for maintenance purposes;

determining that the prior access request is a healthcare access request;

in response to the healthcare access request, enabling an additional function of the infusion device based on the one or more features of the infusion device being restricted.

10. The method of claim 9, wherein the additional function of the infusion device is a secondary authorization requirement for a patient care procedure.

11. The method of claim 8, further comprising:

determining, based on a subsequent reading from the sensor, that the maintenance requirement has been satisfied; and in response to the determination that the maintenance requirement has been satisfied:

unrestricting the one or more features of the infusion device; and transmitting, to the server, a notification indicating that the maintenance requirement has been satisfied.

12. The method of claim 11, wherein the first access request is associated with the technician for maintenance purposes, the method further comprising:

prior to receiving the first access request associated with the technician for maintenance purposes:

receiving a reservation instruction from the server;

restricting access to the infusion device for maintenance purposes only; and in response to the determination that the maintenance requirement has been satisfied:

unrestricting non-maintenance access to the infusion device.

13. The method of claim 8, wherein:

the component is a battery;

the identified maintenance requirement comprises a battery replacement; and the first function is a high-power function of the infusion device.

14. The method of claim 8, wherein:

the component is a wireless network interface;

the identified maintenance requirement comprises a wireless network interface replacement; and the first function is a service sign-off function of the infusion device.

15. The method of claim 8, wherein:

the component is a radio-frequency identification (RFID) reader;

the identified maintenance requirement comprises an RFID reader replacement; and the first function is an access request function of the infusion device.

16. The method of claim 8, wherein:

the component is a pumping mechanism;

the identified maintenance requirement comprises a pumping mechanism replacement; and the first function is a pumping function of the infusion device.

17. The method of claim 8, wherein, while in the healthcare mode, requiring authorization from a clinician different than the user to enable the restricted patient care functions.

18. The method of claim 8, wherein the first access request comprises a login request detected by a badge swipe or a passcode.

19. The method of claim 18, wherein determining that the first access request is a maintenance access request includes determining that the first access request comprises a login request detected by a badge or passcode associated with a maintenance technician.

20. A non-transitory machine-readable storage medium embodying instructions that, when executed by a machine, allow the machine to perform a method comprising:

obtaining a reading from a sensor associated with an infusion device;

detecting, based on the reading from the sensor, a state of a component of a plurality of electronic components in the infusion device;

identifying, based on the detected state of the component, a maintenance requirement of the infusion device and comprising an action to be undertaken by a technician to improve functioning of a component system pertaining to the component;

restricting, responsive to identifying the maintenance requirement, one or more features of the infusion device, including disabling a function of the component, based on the identified maintenance requirement, while maintaining operation of other patient care functions of the infusion device;

transmitting the identified maintenance requirement and an identification of the component to a server over a network;

receiving, from the server over the network, component identification information identifying a replacement part for replacement of the component and guidance for performing maintenance on the infusion device to address the identified maintenance requirement with the replacement part;

receiving, after the one or more features of the infusion device is restricted, an access request of a user;

determining, based on the access request, whether the access request is associated with a technician attempting to gain access to the infusion device for maintenance purposes or a clinician attempting to gain access to the infusion device for patient care purposes; and adjusting the infusion device to one of a healthcare mode and a maintenance mode responsive to the access request, wherein the method further comprises, after the infusion device is adjusted:

responsive to the access request being associated with a technician for maintenance purposes: operating the infusion device in a maintenance mode that restricts patient care functions including operation of a pump or physiological monitor by the user, display the component identification information and the guidance for performing the maintenance with the replacement part on a first user interface of the infusion device, and prevent clearance of the identified maintenance requirement until an identifier for the replacement part is received;

responsive to the access request being associated with the clinician for patient care purposes: operating the infusion device in a healthcare mode that restricts the patient care functions associated with the identified maintenance requirement while patient care functions not requiring use of the component are unrestricted, and display options for providing care with the infusion device on a second user interface of the infusion device different than the first user interface and, while in the healthcare mode, disable the maintenance mode to prevent display of the component identification information and the guidance to the user.

* * * * *